United States Patent
Liu et al.

(10) Patent No.: US 10,434,333 B2
(45) Date of Patent: Oct. 8, 2019

(54) BEAM SHAPING ASSEMBLY FOR NEUTRON CAPTURE THERAPY

(71) Applicant: NEUBORON MEDTECH LTD., Nanjing, Jiangsu (CN)

(72) Inventors: Yuan-hao Liu, Jiangsu (CN); Pei-yi Lee, Jiangsu (CN)

(73) Assignee: NEUBORON MEDTECH LTD., Nanjing, Jiangsu (CN)

( * ) Notice: Subject to any disclaimer, the term of this patent is extended or adjusted under 35 U.S.C. 154(b) by 0 days.

(21) Appl. No.: 16/028,967

(22) Filed: Jul. 6, 2018

(65) Prior Publication Data
US 2018/0311511 A1 Nov. 1, 2018

Related U.S. Application Data

(63) Continuation of application No. PCT/CN2016/111346, filed on Dec. 21, 2016.

(30) Foreign Application Priority Data

Jan. 8, 2016 (CN) .......................... 2016 1 0013472
Jan. 8, 2016 (CN) ...................... 2016 2 0017409 U

(51) Int. Cl.
*A61N 5/10* (2006.01)
*G21K 5/08* (2006.01)
(Continued)

(52) U.S. Cl.
CPC ............. *A61N 5/1042* (2013.01); *A61N 5/10* (2013.01); *A61N 5/1077* (2013.01); *G21K 5/08* (2013.01);
(Continued)

(58) Field of Classification Search
CPC ...... A61N 5/1042; A61N 5/10; A61N 5/1077; A61N 2005/005; A61N 2005/1087;
(Continued)

(56) References Cited

U.S. PATENT DOCUMENTS

| 5,392,319 A | 2/1995 | Eggers |
| 5,870,447 A | 2/1999 | Powell et al. |

(Continued)

FOREIGN PATENT DOCUMENTS

| CN | 101516157 A | 8/2009 |
| CN | 104511096 A | 4/2015 |

(Continued)

OTHER PUBLICATIONS

International Search Report of PCT/CN2016/111346, dated Feb. 22, 2017.

*Primary Examiner* — Nicole M Ippolito
(74) *Attorney, Agent, or Firm* — Locke Lord LLP; Tim Tingkang Xia, Esq.

(57) ABSTRACT

Disclosed is a beam shaping assembly, including a beam inlet; a target, wherein the target has nuclear reaction with the incident proton beam; a moderator adjoining to the target, wherein the neutrons are moderated by the moderator to epithermal neutrons; a reflector surrounding the moderator, and leads the deflected neutrons back to the moderator to enhance the epithermal neutron beam intensity; and a cooling system, wherein the cooling system comprises a first cooling part for cooling target, a second cooling part and a third cooling part connecting with the first cooling part and extending in a direction parallel to the axis of the accelerating tube respectively, the first cooling part connects with the target in a face to face manner, the cooling medium is inputted into the first cooling part from the second cooling part and is outputted from first cooling part through the third cooling part.

20 Claims, 2 Drawing Sheets

(51) Int. Cl.
*H05H 3/06* (2006.01)
*A61N 5/00* (2006.01)

(52) U.S. Cl.
CPC .......... *H05H 3/06* (2013.01); *A61N 2005/005* (2013.01); *A61N 2005/109* (2013.01); *A61N 2005/1087* (2013.01); *A61N 2005/1094* (2013.01); *A61N 2005/1095* (2013.01)

(58) Field of Classification Search
CPC ...... A61N 2005/109; A61N 2005/1094; A61N 2005/1095; G21K 5/08; H05H 3/06
USPC ............................................ 250/492.1, 492.3
See application file for complete search history.

(56) References Cited

U.S. PATENT DOCUMENTS

| | | | |
|---|---|---|---|
| 2013/0129027 A1* | 5/2013 | Pantell ..................... | H05H 3/06 376/158 |
| 2015/0216029 A1 | 7/2015 | Tsuchida | |
| 2017/0062086 A1* | 3/2017 | Park, Jr. ................... | A61N 5/10 |
| 2018/0001112 A1* | 1/2018 | Liu ...................... | A61N 5/1077 |

FOREIGN PATENT DOCUMENTS

| | | |
|---|---|---|
| CN | 205460520 U | 8/2016 |
| CN | 104429168 B | 6/2017 |
| JP | 2006047115 A | 2/2006 |

\* cited by examiner

BEAM SHAPING ASSEMBLY FOR NEUTRON CAPTURE THERAPY

RELATED APPLICATION INFORMATION

This application is a continuation of International Application No. PCT/CN2016/111346, filed on Dec. 21, 2016, which claims priority to Chinese Patent Application No. 201610013472.X, filed on Jan. 8, 2016; Chinese Patent Application No. 201620017409.9, filed on Jan. 8, 2016, the disclosures of which are hereby incorporated by reference.

FIELD OF THE DISCLOSURE

The present disclosure relates generally to a beam shaping assembly, and, more particularly, to a beam shaping assembly for neutron capture therapy.

BACKGROUND OF THE DISCLOSURE

As atomics moves ahead, such radiotherapy as Cobalt-60, linear accelerators and electron beams has been one of major means to cancer therapy. However, conventional photon or electron therapy has been undergone physical restrictions of radioactive rays; for example, many normal tissues on a beam path will be damaged as tumor cells are destroyed. On the other hand, sensitivity of tumor cells to the radioactive rays differs greatly, so in most cases, conventional radiotherapy falls short of treatment effectiveness on radioresistant malignant tumors (such as glioblastoma multiforme and melanoma).

For the purpose of reducing radiation damage to the normal tissue surrounding a tumor site, target therapy in chemotherapy has been employed in the radiotherapy. While for high-radioresistant tumor cells, radiation sources with high RBE (relative biological effectiveness) including such as proton, heavy particle and neutron capture therapy have also developed. Among them, the neutron capture therapy combines the target therapy with the RBE, such as the boron neutron capture therapy (BNCT). By virtue of specific grouping of boronated pharmaceuticals in the tumor cells and precise neutron beam regulation, BNCT is provided as a better cancer therapy choice than conventional radiotherapy.

In the accelerator-based boron neutron capture therapy, the accelerator-based boron neutron capture therapy accelerates proton beams using an accelerator. The proton beam is accelerated to the energy high enough to overcome Coulomb repulsive force of atomic nucleus of the target, and then has a nuclear reaction with the target to generate neutrons. Therefore, in the process of neutron generation, the target will be irradiated by accelerated proton beams in a very high energy level, and the temperature of target will rise significantly, so the working lifetime of the target will be effected.

Therefore, it is really necessary to provide a new technical solution so as to solve the foregoing problem.

The statements in this section merely provide background information related to the present disclosure and may not constitute prior art.

SUMMARY

In order to satisfy the accuracy of the neutron beam quality, an aspect of the present disclosure provides a beam shaping assembly for neutron capture therapy includes: a beam inlet; a target, wherein the target has nuclear reaction with an incident proton beam from the beam inlet to produce neutrons, the neutrons form a neutron beam; a moderator adjoining to the target, wherein the neutrons are moderated by the moderator to epithermal neutron energies; a reflector surrounding the moderator, wherein the reflector leads deflected neutrons back to enhance epithermal neutron beam intensity; a thermal neutron absorber adjoining to the moderator, wherein the thermal neutron absorber is used for absorbing the thermal neutron so as to avoid overdosing in superficial normal tissue during therapy; a radiation shield, set inside the beam shaping assembly, wherein the radiation shield is used for shielding the leaking neutrons and photons so as to reduce the dose in non-radiation region; a beam outlet; and a cooling system, wherein the cooling system comprises a first cooling part for cooling target, a second cooling part and a third cooling part connecting with the first cooling part and extending in a direction parallel to the axis of the accelerating tube respectively, the first cooling part connects with the target in a face to face manner, the cooling medium is inputted into the first cooling part from the second cooling part and is outputted from first cooling part through the third cooling part.

Implementations of this aspect may include one or more of the following features.

More particularly, the accelerating tube comprises an embedding portion and an extending portion, the target is located at the end of the embedding portion, the embedding portion is embedded inside the moderator, the extending portion extends to the outside of the moderator and is surrounded by the reflector, the first cooling part is located between the target and the moderator, the second cooling part and the third cooling part are located inside the beam shaping assembly and extending along a direction parallel to the axis of the accelerating tube to the outside of the embedding portion.

Further, the first cooling part is located at the end of the accelerating tube and contacted to the target in a face to face manner, the second cooling part and the third cooling part are located at the upper and lower sides of the accelerating tube respectively, so as to form a "| . |" shaped cooling system together with the first cooling part.

Further, the second cooling part and third cooling part are both tubular which are made of copper, and both the second cooling part and third cooling part are perpendicular to the contact surface of the target and the first cooling part.

Further, the first cooling part comprises a first contact portion directly contacts to the target, a second contact portion contacts to the moderator, and a cooling slot for the cooling medium which is located between the first contact portion and the second contact portion, the cooling slot has an inputting slot connected with the second cooling part and an outputting slot connected with the third cooling part.

Further, the upper edge of the inputting slot is located above the upper edge of the second cooling part, and the lower edge of the outputting slot is located below the lower edge of the third cooling part.

Further, the moderator comprises at least a tapered section, the moderator comprising a first end and a second end, the tapered section comprising a third end which is located between the first end and the second end, the tapered section comprising a main body which connects to the first end and the third end, the embedding portion is located between the first end and the third end, the first cooling part is located between the target and the third end.

Further, the target comprises a lithium layer, and an anti-oxidation layer located on one side of the lithium layer to prevent the oxidation of the lithium layer.

Further, the first contact portion is made from thermal conductive materials, or materials capable of heat conducting and blistering inhibiting, and the second contact portion is made from materials able to blistering inhibiting.

Further, the anti-oxidation layer is made of Al or stainless steel, when the first contact portion is made of material that capable of heat conducting and blistering inhibiting, the first contact portion is made from any one of Fe, Ta or V, the second contact portion is made from any one of Fe, Ta or V, and the cooling medium is water.

In order to satisfy the accuracy of the neutron beam quality, in another aspect of the present disclosure provides a beam shaping assembly for neutron capture therapy includes: a beam inlet; a target, set inside the accelerating tube, wherein the target has nuclear reaction with the incident proton beam from the beam inlet to produce neutrons, the neutrons form a neutron beam; a moderator, adjoining to the target, wherein the neutrons are moderated by the moderator to epithermal neutron energies; a reflector, surrounding the moderator, wherein the reflector leads the deflected neutrons back to the moderator to enhance the epithermal neutron beam intensity; an accelerating tube, comprising an embedding portion and an extending portion, the target is located at the end of the embedding portion, the embedding portion is embedded inside the moderator, the extending portion extends to the outside of the moderator and is surrounded by the reflector; a thermal neutron absorber, adjoining to the moderator, wherein the thermal neutron absorber is used for absorbing the thermal neutron so as to avoid overdosing in superficial normal tissue during therapy; a radiation shield, set inside the beam shaping assembly, wherein the radiation shield is used for shielding the leakage of neutrons and photons so as to reduce the dose in non-radiation region; a beam outlet; and a cooling system, comprising a first cooling part for cooling target, a second cooling part and a third cooling part respectively connecting with the first cooling part and extending in a direction parallel to the axis of the accelerating tube, the first cooling part is located between the target and the moderator, the second cooling part comprises a first portion and a second portion extends from the first portion, the third cooling part comprises a third portion and a fourth portion extends from the third portion, the first portion and the third portion are connected with the first cooling part and embedded inside the moderator together with the embedding portion of the accelerating tube, the second portion and the fourth portion extend to the outside of the moderator along the extending portion of the accelerating tube.

Further, the first cooling part comprises a first contact portion directly contacts to the target, a second contact portion contacts to the moderator, and a cooling slot for the cooling medium which is located between the first contact portion and the second contact portion, the cooling slot has an inputting slot connected with the second cooling part and an outputting slot connected with the third cooling part.

Further, the second cooling part and the third cooling part are located at the upper and lower sides of embedding portion, the first portion connects with the inputting slot, the third portion connects with the outputting slot.

Further, the second cooling part and third cooling part are both tubular which are made of copper, and both the second cooling part and third cooling part are perpendicular to the contact surface of the target and the first cooling part, so as to form a "⌐" shaped cooling system.

Further, the upper edge of the inputting slot is located above the upper edge of the second cooling part, and the lower edge of the outputting slot is located below the lower edge of the third cooling part.

Further, the moderator comprises at least a tapered section, the moderator comprising a first end and a second end, the tapered section defines a third end which is located between the first end and the second end, the tapered section comprising a main body which connects with the first end and the third end; the first cooling part and the first portion and the third portion are embedded inside the main body and located between the first end and the third end, the cooling medium is inputted into the first cooling part from the second cooling part and is outputted from the first cooling part through the third cooling part.

In order to satisfy the accuracy of the neutron beam quality, in another aspect of the present disclosure provides a beam shaping assembly for neutron capture therapy includes: a beam inlet; a target, set inside the accelerating tube, wherein the target has nuclear reaction with the incident proton beam from the beam inlet to produce neutrons, the neutrons form a neutron beam; a moderator, adjoining to the target, wherein the neutrons are moderated by the moderator to epithermal neutron energies; a reflector, surrounding the moderator, wherein the reflector leads the deflected neutrons back to the moderator to enhance the epithermal neutron beam intensity; a thermal neutron absorber, adjoining to the moderator, wherein the thermal neutron absorber is used for absorbing the thermal neutron so as to avoid overdosing in superficial normal tissue during therapy; a radiation shield, set inside the beam shaping assembly, wherein the radiation shield is used for shielding the leakage of neutrons and photons so as to reduce the dose in non-radiation region; a beam outlet; and a cooling system, comprising a first cooling part for cooling target, a second cooling part and a third cooling part located inside the beam shaping assembly and extending along a direction parallel to the axis of the accelerating tube, the first cooling part comprises a first contact portion directly contacts to the target and a second contact portion contacts to the moderator, and a cooling slot for the cooling medium is located between the first contact portion and the second contact portion, the cooling slot has an inputting slot connected with the second cooling part and an outputting slot connected with the third cooling part, the cooling medium is inputted into the first cooling part from the second cooling part and is outputted from the first cooling part through the third cooling part, the upper edge of the inputting slot is located above the upper edge of the second cooling part, and the lower edge of the outputting slot is located below the lower edge of the third cooling part.

Further, the target comprises a lithium layer, and an anti-oxidation layer located on one side of the lithium layer to prevent the oxidation of the lithium layer.

Further, the first contact portion is made from thermal conductive materials, or materials capable of heat conducting and blistering inhibiting, and the second contact portion is made from materials able to blistering inhibiting.

Further, the anti-oxidation layer is made of Al or stainless steel, when the first contact portion is made of material that capable of heat conducting and blistering inhibiting, the first contact portion is made from any one of Fe, Ta or V, the second contact portion is made from any one of Fe, Ta or V, and the cooling medium is water.

Further areas of applicability will become apparent from the description provided herein. It should be understood that the description and specific examples are intended for purposes of illustration only and are not intended to limit the scope of the present disclosure.

DETAILED DESCRIPTION

Figure 1:
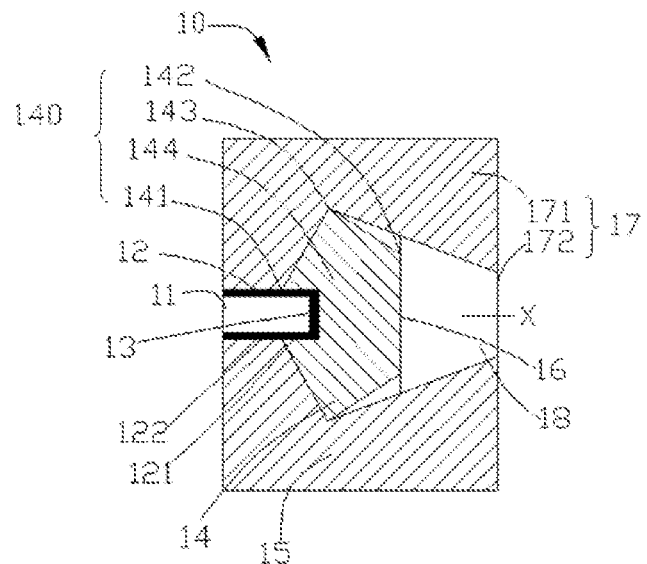
FIG. 1 is a schematic view for the beam shaping assembly for neutron capture therapy of the present disclosure.

The following description of the preferred embodiments is merely exemplary in nature and is in no way intended to limit the invention, its application, or uses.

Neutron capture therapy (NCT) has been increasingly practiced as an effective cancer curing means in recent years, and BNCT is the most common. Neutrons for NCT may be supplied by nuclear reactors or accelerators. Take AB-BNCT for example, its principal components comprise, in general, an accelerator for accelerating charged particles (such as protons and deuterons), a target, a heat removal system and a beam shaping assembly. The accelerated charged particles interact with the metal target to produce the neutrons, and suitable nuclear reactions are always determined according to such characteristics as desired neutron yield and energy, available accelerated charged particle energy and current and materialization of the metal target, among which the most discussed two are $^7$Li (p, n) $^7$Be and $^9$Be (p, n) $^9$B and both are endothermic reaction. Their energy thresholds are 1.881 MeV and 2.055 MeV respectively. Epithermal neutrons at a keV energy level are considered ideal neutron sources for BNCT. Theoretically, bombardment with lithium target using protons with energy slightly higher than the thresholds may produce neutrons relatively low in energy, so the neutrons may be used clinically without many moderations. However, Li (lithium) and Be (beryllium) and protons of threshold energy exhibit not high action cross section. In order to produce sufficient neutron fluxes, high-energy protons are usually selected to trigger the nuclear reactions.

The target, considered perfect, is supposed to have the advantages of high neutron yield, a produced neutron energy distribution near the epithermal neutron energy range (see details thereinafter), little strong-penetration radiation, safety, low cost, easy accessibility, high temperature resistance etc. But in reality, no nuclear reactions may satisfy all requests. The target in these embodiments of the present disclosure is made of lithium. However, well known by those skilled in the art, the target materials may be made of other metals besides the above-mentioned.

Requirements for the heat removal system differ as the selected nuclear reactions. $^7$Li (p, n) $^7$Be asks for more than $^9$Be (p, n) $^9$B does because of low melting point and poor thermal conductivity coefficient of the metal (lithium) target. In these embodiments of the present disclosure is $^7$Li (p, n) $^7$Be. It can be seen that, the temperature of the target after being irradiated by accelerated proton beam in high energy level will certainly rise significantly, so working lifetime of the target will be influenced.

No matter BNCT neutron sources are from the nuclear reactor or the nuclear reactions between the accelerator charged particles and the target, only mixed radiation fields are produced, that is, beams comprise neutrons and photons having energies from low to high. As for BNCT in the depth of tumors, except the epithermal neutrons, the more the residual quantity of radiation ray is, the higher the proportion of nonselective dose deposition in the normal tissue is. Therefore, radiation causing unnecessary dose should be lowered down as much as possible. Besides air beam quality factors, dose is calculated using a human head tissue prosthesis in order to understand dose distribution of the neutrons in the human body. The prosthesis beam quality factors are later used as design reference to the neutron beams, which is elaborated hereinafter.

The International Atomic Energy Agency (IAEA) has given five suggestions on the air beam quality factors for the clinical BNCT neutron sources. The suggestions may be used for differentiating the neutron sources and as reference for selecting neutron production pathways and designing the beam shaping assembly, and are shown as follows:

Epithermal neutron flux>$1 \times 10^9$ n/cm$^2$s
Fast neutron contamination<$2 \times 10^{-13}$ Gy-cm$^2$/n
Photon contamination<$2 \times 10^{-13}$ Gy-cm$^2$/n
Thermal to epithermal neutron flux ratio<0.05
Epithermal neutron current to flux ratio>0.7

Note: the epithermal neutron energy range is between 0.5 eV and 40 keV, the thermal neutron energy range is lower than 0.5 eV, and the fast neutron energy range is higher than 40 keV.

1. Epithermal Neutron Flux

The epithermal neutron flux and the concentration of the boronated pharmaceuticals at the tumor site codetermine clinical therapy time. If the boronated pharmaceuticals at the tumor site are high enough in concentration, the epithermal neutron flux may be reduced. On the contrary, if the concentration of the boronated pharmaceuticals in the tumors is at a low level, it is required that the epithermal neutrons in the high epithermal neutron flux should provide enough doses to the tumors. The given standard on the epithermal neutron flux from IAEA is more than $10^9$ epithermal neutrons per square centimeter per second. In this flux of neutron beams, therapy time may be approximately controlled shorter than an hour with the boronated pharmaceuticals. Thus, except that patients are well positioned and feel more comfortable in shorter therapy time, and limited residence time of the boronated pharmaceuticals in the tumors may be effectively utilized.

2. Fast Neutron Contamination

Unnecessary dose on the normal tissue produced by fast neutrons are considered as contamination. The dose exhibit positive correlation to neutron energy, hence, the quantity of the fast neutrons in the neutron beams should be reduced to the greatest extent. Dose of the fast neutrons per unit epithermal neutron flux is defined as the fast neutron contamination, and according to IAEA, it is supposed to be less than $2*10^{-13}$ Gy-cm$^2$/n.

3. Photon Contamination (Gamma-Ray Contamination)

Gamma-ray long-range penetration radiation will selectively result in dose deposit of all tissues in beam paths, so that lowering the quantity of gamma-ray is also the exclusive requirement in neutron beam design. Gamma-ray dose accompanied per unit epithermal neutron flux is defined as gamma-ray contamination which is suggested being less than $2*10^{-13}$ Gy-cm$^2$/n according to IAEA.

4. Thermal to Epithermal Neutron Flux Ratio

The thermal neutrons are so fast in rate of decay and poor in penetration that they leave most of energy in skin tissue after entering the body. Except for skin tumors like melanocytoma, the thermal neutrons serve as neutron sources of BNCT, in other cases like brain tumors, the quantity of the thermal neutrons has to be lowered. The thermal to epithermal neutron flux ratio is recommended at lower than 0.05 in accordance with IAEA.

5. Epithermal Neutron Current to Flux Ratio

The epithermal neutron current to flux ratio stands for beam direction, the higher the ratio is, the better the forward direction of the neutron beams is, and the neutron beams in the better forward direction may reduce dose surrounding the normal tissue resulted from neutron scattering. In addition, treatable depth as well as positioning posture is improved. The epithermal neutron current to flux ratio is better of larger than 0.7 according to IAEA.

In order to achieve a better quality of neutron beam and solve the target cooling problem at the same time, the present disclosure provides a beam shaping assembly 10 used for neutron capture therapy. A cooling system 20 is arranged inside the beam shaping assembly 10 to cool down the temperature of the target.

As shown in FIG. 1, the beam shaping assembly 10 includes a beam inlet 11, an accelerating tube 12 located inside the beam shaping assembly 10, a target 13 set inside the accelerating tube 12, a moderator 14 adjoining to the target 13, a reflector 15 surrounding outside the moderator 14, a thermal neutron absorber 16 adjoining to the moderator 14, a radiation shield 17 set inside the beam shaping assembly 10, and a beam outlet 18. The target 13 has a nuclear reaction with incident proton beam from the beam inlet 11 to generate neutrons, the neutrons form a neutron beam. The neutron beam defines an axis X. The neutrons are moderated by the moderator to epithermal neutron energies. The reflector 15 leads the neutrons deviating from the axis X back to the moderator 14 to increase the epithermal neutron beam intensity. The thermal neutron absorber 16 is used for thermal neutron absorption to avoid overdosing towards superficial normal tissues during the therapy. The radiation shield 17 is used for shielding the leaking neutron and photon to reduce the dose towards normal tissues in the non-radiation region.

The accelerator-based boron neutron capture therapy uses an accelerator to accelerate the proton beam, as a preferred embodiment, the target 13 is made of lithium. The proton beam is accelerated enough to overcome Coulomb repulsive force of the target atomic nucleus and has a $^7$Li(p,n)$^7$Be nuclear reaction with target 13 to generate neutrons. The beam shaping assembly 10 slows down the neutrons to epithermal neutron energies, and reduces thermal neutrons and fast neutrons.

The moderator 14 is made of the material which has a large cross-section of fast neutron reaction and a small reaction cross-section of epithermal neutron. The reflector 15 is made of the material which has strong neutron reflecting capability. The thermal neutron absorber 16 is made of the material which has large cross-section of thermal neutron reaction. As one preferred embodiment, moderator 14 is made of at least one of $D_2O$, $AlF_3$, Fluental™, $CaF_2$, $Li_2CO_3$, $MgF_2$ and $Al_2O_3$, and reflector 15 is made of at least one of Pb or Ni, and thermal neutron absorber 16 is made of $^6$Li. The radiation shield 17 includes photon shield 171 and neutron shield 172, as one preferred embodiment, the radiation shield 17 includes photon shield 171 which is made of plumbum (Pb) and neutron shield 172 which is made of polyethylene (PE).

The accelerating tube 12 includes an embedding portion 121 and an extending portion 122, the target 13 set at the end of the embedding portion 121 of the accelerating tube 12. The embedding portion 121 is embedded inside the moderator 14, and the extending portion 122 extends to the outer side of the moderator 14 and is surrounded by reflector 15. In the present embodiment, accelerating tube 12 is embedded inside the moderator 14. In order to make sure that a better quality of neutron beam can be achieved from the beam shaping assembly 10 during the cooling of target 13 by the cooling system 20 embedded in the accelerating tube 12, the cooling system 20 is set as follows.

Figure 2:
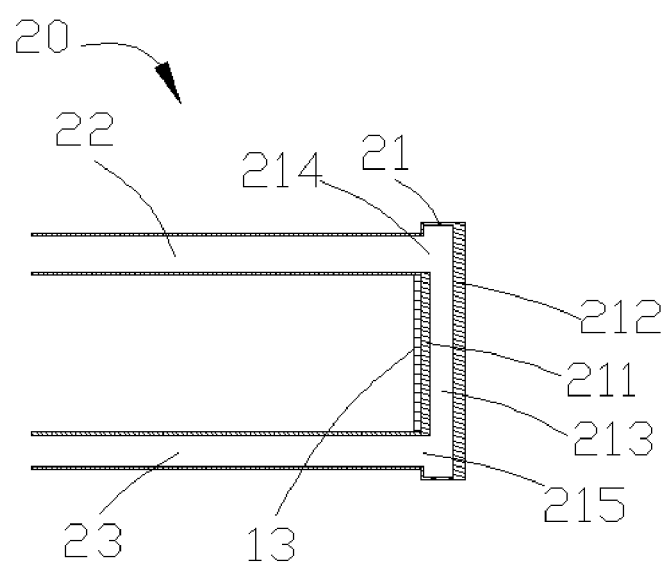
FIG. 2 is a schematic view for the cooling system of "⊐" shaped structure of the present disclosure

The cooling system 20 includes a first cooling part 21 for the cooling of target 13, a second cooling part 22 and a third cooling part 23 extend along the direction of the axis of accelerating tube 12 and located on both sides of accelerating tube 12, cooling medium is inputted into the first cooling part 21 from the second cooling part 22 and is outputted outside the first cooling part 21 from the third cooling part 23. The first cooling part 21 is located between the target 13 and the moderator 14, one side of the first cooling part 21 connects with target 13 and the other side of the first cooling part 21 connects with the moderator 14. The second cooling part 22 and third cooling part 23 extend from the outer side of the extending portion 122 to the outer side of embedding portion 121 and separately connected to the first cooling part 21 and located inside the moderator 14 at the same time. In other words, the first cooling part 21 is located on the end of embedding portion 121, and also on one side of the target 13, and directly connects with the target 13. The second cooling part 22 and third cooling part 23 are located on the upper and lower side of accelerating tube 12 respectively, and are separately connected with the first cooling part 21, therefore the whole cooling system 20 is arranged as a "⊏" shape. In the present embodiment, the first cooling part 21 has a face to face connect with the target 13, the second cooling part 22 and the third cooling part 23 are both tubular structures made of copper, both the second cooling part 22 and third cooling part 23 are perpendicular to a plane where the first cooling part 21 and target 13 are connected (combined with FIG. 2).

The first cooling part 21 includes a first contact portion 211, a second contact portion 212 and a cooling slot 213 for cooling medium which is located between the first contact portion 211 and the second contact portion 212. The first contact portion 211 is directly contacted to the target 13, and the second contact portion 212 is directly contacted to moderator 14 or indirectly contacted to moderator 14 through air. The cooling slot 213 has an inputting slot 214 connected with the second cooling part 22 and an outputting slot 215 connected with the third cooling part 23. The first contact portion 211 is made of thermal conductive materials. The upper edge of the inputting slot 214 is located above the upper edge of second cooling part 22, and the lower edge of the outputting slot 215 is located below the lower edge of third cooling part 23. The benefits of such arrangement are that the cooling medium can be more easily inputted into cooling slot 213 and the temperature of target 13 can be cooled down in a timelier manner, the cooling medium can be more easily outputted outside the cooling slot 213 after heated, the pressure of cooling water in cooling slot 213 can also in some degree be reduced.

Figure 3:
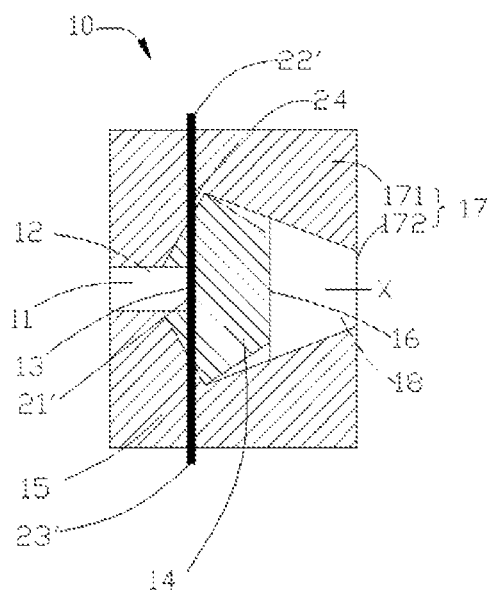
FIG. 3 is a schematic view for the cooling system of "I" shaped structure of the present disclosure.
Figure 4:
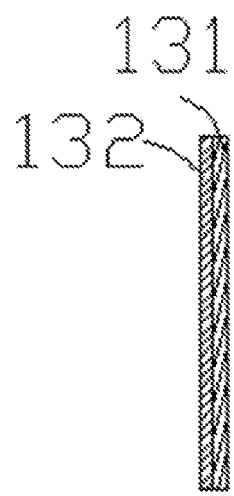
FIG. 4 is a schematic view for the target structure of the present disclosure.

Obviously, the cooling system can also be arranged as I shape to cool target 13 in an embedded accelerating tube 12. The arrangement of the first cooling part 21' of "I" shaped cooling system 20 is the same as the first cooling part 21 in "⊏" shaped cooling system 20. The differences are that, the second cooling part 22' and third cooling part 23' of the I shape cooling system 20 are located in the same plane with the first cooling part 21', the second cooling part 22' and third cooling part 23 are extended out of the moderator 14 respectively along the direction perpendicular to the axis of the accelerating tube 12, the referred "I" shaped structure (as shown in FIG. 3). Although "I" shaped cooling system is also useful for the cooling of target 13, a slot 24 must be set on the moderator 14 for the arrangement of second cooling part 22' and third cooling part 23', and the assembly of the cooling system is complex. And the more important is that the neutron flux and the air beam quality factors are worse than that of the "⊏" shaped cooling system 20.

Now, take a moderator 14 made of $AlF_3$ (2.78 g/cm) for example. The followings are analog computation of "⊏" shaped and "I" shaped cooling system arranged in the beam shaping assembly by MCNP software (a common-use software package developed by Los Alamos National Laboratory of the United States for computing neutrons, photons, charged particles or transporting coupled neutrons/photons/charged particles in 3D complicated geometric structures):

Table 1 as follow shows the performances of air beam quality factors in the two embodiments (each item in the table is calculated in the same unit above, so not repeat here and similarly hereinafter):

TABLE 1

Air Beam Quality Factors

| | shape of cooling system | |
|---|---|---|
| Air beam quality factors | "⊏" shaped | "I" shaped |
| epithermal neutron flux ($n/cm^2$-mA) | 1.22E+08 | 9.97E+07 |
| fast neutron contamination ($Gy-cm^2/n$) | 3.47E−13 | 3.41E−13 |
| Photon contamination ($Gy-cm^2/n$) | 1.11E−13 | 1.97E−13 |
| thermal to epithermal neutron flux ratio | 0.02 | 0.05 |
| epithermal neutron current to flux ratio | 0.70 | 0.71 |

Note:
In order to conservatively estimate the epithermal neutron flux and fast neutron contamination, in the examples, the epithermal neutron range is 0.5 eV-10 keV, the thermal neutron range is <0.5 eV, and the fast neutron range is >10 keV.

Table 2 as follow shows the performance of neutron flux in the two embodiments:

TABLE 2 neutron flux ($n/cm^2$-mA)

| | shape of cooling system | |
|---|---|---|
| neutron flux | "⊏" shaped | "I" shaped |
| thermal neutron flux (thermal neutron flux/total neutron flux) | 2.53E+06 (2%) | 4.52E+06 (4%) |
| epithermal neutron flux (epithermal neutron flux/total neutron flux) | 1.22E+08 (85%) | 9.97E+07 (84%) |

TABLE 2-continued neutron flux ($n/cm^2$-mA)

| | shape of cooling system | |
|---|---|---|
| neutron flux | "⊏" shaped | "I" shaped |
| fast neutron flux (fast neutron flux/total neutron flux) | 1.89E+07 (13%) | 1.47E+07 (12%) |
| total neutron flux | 1.44E+08 (100%) | 1.19E+08 (100%) |

Note:
In order to conservatively estimate the epithermal neutron flux and fast neutron contamination, in the examples, the epithermal neutron range is 0.5 eV-10 keV, the thermal neutron range is <0.5 eV, and the fast neutron range is >10 keV.

The target 13 includes a lithium layer 131 and an anti-oxidation layer 132 located on one side of lithium layer 131 to prevent the oxidation of lithium layer 131. The anti-oxidation layer 132 is made of Al or stainless steel. The first contact portion 211 is made of materials having high thermal conductivity (such as Cu, Fe, Al etc.) or materials having high thermal conductivity and good blistering resistant ability, the second contact portion 211 is made of blistering resistant materials. The blistering resistant materials or materials having high thermal conductivity as well as good blistering resistant ability is made of any one of Fe, Ta or V. The temperature of target 13 rises up after being irradiated by accelerated proton beam in high energy level, and as the flowing of the cooling medium in the cooling slot 23, the heat is brought away by the first contact portion 211, and the temperature of the target is cooled down. In the present embodiment, the cooling medium is water.

As a preferred embodiment, the moderator 14 is arranged as a structure including at least one tapered section 140. The moderator 14 includes a first end 141 and a second end 142. The tapered section 140 includes a third end 143 located between the first end 141 and the second end 142, and main body part 144 connects with the first end 141 and the third end 143. The embedding section 121 of accelerating tube 12 is located between the first end 141 and the third end 143 of tapered section 140. The first cooling part 21 is located between target 13 and the third end 143. The benefits of such an arrangement are that, the moderator 14 can be controlled in a quite reasonable size, and the beam shaping assembly can achieve a better effect of moderation as well as a better neutron beam quality. Specifically, since the first cooling part 21 is located between the target 13 and the third end 143, the moderator 14 behind the third end 143 moderates the better forward directional characteristics and higher energy neutrons to epithermal neutron energies. In other words, such an arrangement enables the moderator to have enough size for the neutrons with better forward directional characteristics and higher energy, so that the neutrons are moderated sufficiently. After being moderated by the main body 144, part of the neutrons deviating from the axis X, the reflector 15 leads the deflected neutrons back to the axis X in a certain angle because of the tapered section of moderator. And the tapered section can avoid the excessively moderating of lower energy neutrons on the route of reflecting back to the axis X. Therefore, the tapered section can achieve a good moderation for neutrons with better forward directional characteristics, and maintain the intensity of lower energy neutrons at the same time, so as to achieve a better neutron beam quality.

The term 'tapered' or 'tapered section' or 'tapered structure' referred in the embodiment of the present disclosure is an element with the contour in a tapering trend from one to the other side along the illustrated direction. One of contour lines may be a line segment, like a corresponding one of the cone, or may be an arc, like a corresponding one of the sphere, and the integral surface of the contour may be continuously connected or not if the surface of the cone shape or the spherical shape is provided with plenty of protrusions and grooves.

The above illustrates and describes basic principles, main features and advantages of the present disclosure. Those skilled in the art should appreciate that the above embodiments do not limit the present disclosure in any form. Technical solutions obtained by equivalent substitution or equivalent variations all fall within the scope of the present disclosure.

What is claimed is:

1. A beam shaping assembly for neutron capture therapy, the neutron capture therapy comprising an accelerating tube for accelerating the proton beam, the beam shaping assembly comprising:
    a beam inlet;
    a target, wherein the target has nuclear reaction with an incident proton beam from the beam inlet to produce neutrons, the neutrons form a neutron beam;
    a moderator adjoining to the target, wherein the neutrons are moderated by the moderator to epithermal neutron energies;
    a reflector surrounding the moderator, wherein the reflector leads deflected neutrons back to enhance epithermal neutron beam intensity;
    a thermal neutron absorber adjoining to the moderator, wherein the thermal neutron absorber is used for absorbing the thermal neutron so as to avoid overdosing in superficial normal tissue during therapy;
    a radiation shield, set inside the beam shaping assembly, wherein the radiation shield is used for shielding the leaking neutrons and photons so as to reduce the dose in non-radiation region;
    a beam outlet; and
    a cooling system, wherein the cooling system comprises a first cooling part for cooling target, a second cooling part and a third cooling part connecting with the first cooling part and extending in a direction parallel to the axis of the accelerating tube respectively, the first cooling part connects with the target in a face to face manner, the cooling medium is inputted into the first cooling part from the second cooling part and is outputted from first cooling part through the third cooling part.

2. The beam shaping assembly for neutron capture therapy according to claim 1, wherein the accelerating tube comprises an embedding portion and an extending portion, the target is located at the end of the embedding portion, the embedding portion is embedded inside the moderator, the extending portion extends to the outside of the moderator and is surrounded by the reflector, the first cooling part is located between the target and the moderator, the second cooling part and the third cooling part are located inside the beam shaping assembly and extending along a direction parallel to the axis of the accelerating tube to the outside of the embedding portion.

3. The beam shaping assembly for neutron capture therapy according to claim 2, wherein the moderator comprises at least a tapered section, the moderator comprising a first end and a second end, the tapered section comprising a third end which is located between the first end and the second end, the tapered section comprising a main body which connects to the first end and the third end, the embedding portion is located between the first end and the third end, the first cooling part is located between the target and the third end.

4. The beam shaping assembly for neutron capture therapy according to claim 1, wherein the first cooling part is located at the end of the accelerating tube and contacted to the target in a face to face manner, the second cooling part and the third cooling part are located at the upper and lower sides of the accelerating tube respectively, so as to form a "⊏" shaped cooling system together with the first cooling part.

5. The beam shaping assembly for neutron capture therapy according to claim 1, wherein the second cooling part and third cooling part are both tubular which are made of copper, and both the second cooling part and third cooling part are perpendicular to the contact surface of the target and the first cooling part.

6. The beam shaping assembly for neutron capture therapy according to claim 1, wherein the first cooling part comprises a first contact portion directly contacts to the target, a second contact portion contacts to the moderator, and a cooling slot for the cooling medium which is located between the first contact portion and the second contact portion, the cooling slot has an inputting slot connected with the second cooling part and an outputting slot connected with the third cooling part.

7. The beam shaping assembly for neutron capture therapy according to claim 6, wherein the upper edge of the inputting slot is located above the upper edge of the second cooling part, and the lower edge of the outputting slot is located below the lower edge of the third cooling part.

8. The beam shaping assembly for neutron capture therapy according to claim 6, wherein the target comprises a lithium layer, and an anti-oxidation layer located on one side of the lithium layer to prevent the oxidation of the lithium layer.

9. The beam shaping assembly for neutron capture therapy according to claim 8, wherein the anti-oxidation layer is made of Al or stainless steel, when the first contact portion is made of material that capable of heat conducting and blistering inhibiting, the first contact portion is made from any one of Fe, Ta or V, the second contact portion is made from any one of Fe, Ta or V, and the cooling medium is water.

10. The beam shaping assembly for neutron capture therapy according to claim 6, wherein the first contact portion is made from thermal conductive materials, or materials capable of heat conducting and blistering inhibiting, and the second contact portion is made from materials able to blistering inhibiting.

11. A beam shaping assembly for neutron capture therapy, the neutron capture therapy comprising an accelerating tube for accelerating the proton beam, the beam shaping assembly comprising:
    a beam inlet;
    a target, set inside the accelerating tube, wherein the target has nuclear reaction with the incident proton beam from the beam inlet to produce neutrons, the neutrons form a neutron beam;
    a moderator, adjoining to the target, wherein the neutrons are moderated by the moderator to epithermal neutron energies;
    a reflector, surrounding the moderator, wherein the reflector leads the deflected neutrons back to the moderator to enhance the epithermal neutron beam intensity;
    a thermal neutron absorber, adjoining to the moderator, wherein the thermal neutron absorber is used for absorbing the thermal neutron so as to avoid overdosing in superficial normal tissue during therapy;

a radiation shield, set inside the beam shaping assembly, wherein the radiation shield is used for shielding the leakage of neutrons and photons so as to reduce the dose in non-radiation region;

a beam outlet; and a cooling system, comprising a first cooling part for cooling target, a second cooling part and a third cooling part respectively connecting with the first cooling part and extending in a direction parallel to the axis of the accelerating tube, the first cooling part is located between the target and the moderator, the second cooling part comprises a first portion and a second portion extends from the first portion, the third cooling part comprises a third portion and a fourth portion extends from the third portion;

wherein the accelerating tube comprises an embedding portion and an extending portion, the target is located at the end of the embedding portion, the embedding portion is embedded inside the moderator, the extending portion extends to the outside of the moderator and is surrounded by the reflector;

wherein the first portion and the third portion are connected with the first cooling part and embedded inside the moderator together with the embedding portion of the accelerating tube, the second portion and the fourth portion extend to the outside of the moderator along the extending portion of the accelerating tube.

12. The beam shaping assembly for neutron capture therapy according to claim 11, wherein the first cooling part comprises a first contact portion directly contacts to the target, a second contact portion contacts to the moderator, and a cooling slot for the cooling medium which is located between the first contact portion and the second contact portion, the cooling slot has an inputting slot connected with the second cooling part and an outputting slot connected with the third cooling part.

13. The beam shaping assembly for neutron capture therapy according to claim 12, wherein the second cooling part and the third cooling part are located at the upper and lower sides of embedding portion, the first portion connects with the inputting slot, the third portion connects with the outputting slot.

14. The beam shaping assembly for neutron capture therapy according to claim 13, wherein the upper edge of the inputting slot is located above the upper edge of the second cooling part, and the lower edge of the outputting slot is located below the lower edge of the third cooling part.

15. The beam shaping assembly for neutron capture therapy according to claim 11, wherein the second cooling part and third cooling part are both tubular which are made of copper, and both the second cooling part and third cooling part are perpendicular to the contact surface of the target and the first cooling part, so as to form a "⊏" shaped cooling system.

16. The beam shaping assembly for neutron capture therapy according to claim 11, wherein the moderator comprises at least a tapered section, the moderator comprising a first end and a second end, the tapered section defines a third end which is located between the first end and the second end, the tapered section comprising a main body which connects with the first end and the third end; the first cooling part and the first portion and the third portion are embedded inside the main body and located between the first end and the third end, the cooling medium is inputted into the first cooling part from the second cooling part and is outputted from the first cooling part through the third cooling part.

17. A beam shaping assembly for neutron capture therapy, the neutron capture therapy comprising an accelerating tube for accelerating the proton beam, the beam shaping assembly comprising:

a beam inlet;

a target, set inside the accelerating tube, wherein the target has nuclear reaction with the incident proton beam from the beam inlet to produce neutrons, the neutrons form a neutron beam;

a moderator, adjoining to the target, wherein the neutrons are moderated by the moderator to epithermal neutron energies;

a reflector, surrounding the moderator, wherein the reflector leads the deflected neutrons back to the moderator to enhance the epithermal neutron beam intensity;

a thermal neutron absorber, adjoining to the moderator, wherein the thermal neutron absorber is used for absorbing the thermal neutron so as to avoid overdosing in superficial normal tissue during therapy;

a radiation shield, set inside the beam shaping assembly, wherein the radiation shield is used for shielding the leakage of neutrons and photons so as to reduce the dose in non-radiation region;

a beam outlet; and a cooling system, comprising a first cooling part for cooling target, a second cooling part and a third cooling part located inside the beam shaping assembly and extending along a direction parallel to the axis of the accelerating tube, the first cooling part comprises a first contact portion directly contacts to the target and a second contact portion contacts to the moderator, and a cooling slot for the cooling medium is located between the first contact portion and the second contact portion, the cooling slot has an inputting slot connected with the second cooling part and an outputting slot connected with the third cooling part, the cooling medium is inputted into the first cooling part from the second cooling part and is outputted from the first cooling part through the third cooling part, the upper edge of the inputting slot is located above the upper edge of the second cooling part, and the lower edge of the outputting slot is located below the lower edge of the third cooling part.

18. The beam shaping assembly for neutron capture therapy according to claim 17, wherein the target comprises a lithium layer, and an anti-oxidation layer located on one side of the lithium layer to prevent the oxidation of the lithium layer.

19. The beam shaping assembly for neutron capture therapy according to claim 18, wherein the anti-oxidation layer is made of Al or stainless steel, when the first contact portion is made of material that capable of heat conducting and blistering inhibiting, the first contact portion is made from any one of Fe, Ta or V, the second contact portion is made from any one of Fe, Ta or V, and the cooling medium is water.

20. The beam shaping assembly for neutron capture therapy according to claim 17, wherein the first contact portion is made from thermal conductive materials, or materials capable of heat conducting and blistering inhibiting, and the second contact portion is made from materials able to blistering inhibiting.

* * * * *